United States Patent [19]

Rosencwaig et al.

[11] Patent Number: 4,522,510
[45] Date of Patent: Jun. 11, 1985

[54] THIN FILM THICKNESS MEASUREMENT WITH THERMAL WAVES

[75] Inventors: Allan Rosencwaig, Danville; Jon Opsal, Livermore, both of Calif.

[73] Assignee: Therma-Wave, Inc., Fremont, Calif.

[21] Appl. No.: 481,275

[22] Filed: Apr. 1, 1983

Related U.S. Application Data

[63] Continuation-in-part of Ser. No. 401,511, Jul. 26, 1982.

[51] Int. Cl.³ .................. G01N 21/41; G01N 25/72
[52] U.S. Cl. ............................ 374/7; 356/43; 356/376; 356/381; 374/5; 374/57
[58] Field of Search ............... 374/117, 57, 4, 5; 356/376, 371

[56] References Cited

U.S. PATENT DOCUMENTS

| | | | |
|---|---|---|---|
| 3,413,474 | 11/1968 | Freeh | 374/7 |
| 3,667,846 | 6/1972 | Nater et al. | 356/376 X |
| 3,733,052 | 3/1969 | Maley | 374/7 X |
| 3,828,126 | 4/1973 | Ramsey, Jr. | 356/376 X |
| 3,938,365 | 2/1976 | Dewey, Jr. | 73/24 |
| 3,978,713 | 9/1976 | Penny | 73/643 X |
| 4,014,613 | 3/1977 | Sharp, Jr. | 374/55 |
| 4,137,778 | 2/1979 | Primbsch | 73/643 |
| 4,254,337 | 3/1981 | Yasujima et al. | 250/341 X |
| 4,255,971 | 3/1981 | Rosencwaig | 374/117 X |
| 4,271,705 | 6/1981 | Crostack | 73/602 |
| 4,274,288 | 6/1981 | Tittmann et al. | 73/602 X |
| 4,299,494 | 11/1981 | Badoz et al. | 374/45 X |
| 4,305,294 | 12/1981 | Vasile et al. | 73/602 X |
| 4,468,136 | 8/1984 | Murphy et al. | 374/45 |

OTHER PUBLICATIONS

"Photoacoustic Effect as a Liquid Absorbance Detector", A. Atalar, Applied Optics/ vol. 19, No. 8, Sep. 15, 1980, (p. 3204–310).
Publ. "Photoacoustics & Photoacoustic Spectroscophy, pp. 270-284, vol. 57, Allan Rosencwaig, A Wiley-Interscience Publication, 1941, 1980 ®.
Publ. "Scanning Acoustic Microscopy", p. 37-43, Weglein et al., 15, A. P. Reliability Physics, Los Vegas Nev., Apr. 12-14, 1977.
Publ. "Oblique Incidence Reflection Acoustic Imaging, Yeack et al., May 27, 1980 (J. Appl. Phys. 51(9), 9/1980), pp. 4637–4644.

Primary Examiner—Daniel M. Yasich
Attorney, Agent, or Firm—Limbach, Limbach & Sutton

[57] ABSTRACT

A method and apparatus for thin film thickness measurements with thermal waves in which heating and detection laser beams are focused onto the film, normal to the surface of the film, with the two beams parallel and non-coaxial.

20 Claims, 5 Drawing Figures

THIN FILM THICKNESS MEASUREMENT WITH THERMAL WAVES

RELATED APPLICATIONS

This application is a continuation-in-part of copending application Ser. No. 401,511, filed July 26, 1982, incorporated herein by reference.

BACKGROUND OF INVENTION

It is well known from photoacoustic theory (A. Rosencwaig and A. Gersho, J. Appl. Phys. 47, 64 (1976) and A. Rosencwaig, *Photoacoustics and Photoacoustic Spectroscopy*, Wiley, Interscience, New York, 1980) that one can, with thermal waves, obtain information about the thermal characteristics of a sample as a function of depth beneath its surface. Thermal characteristics or features are those regions of an otherwise homogeneous material that exhibit variations relative to their surroundings in thermal conductivity, thermal expansion coefficient or volume specific heat. Variations in these thermal parameters can arise from changes in basic material composition or from the presence of mechanical defects such cracks, voids and delaminations. Variations in thermal parameters can also arise from changes in the crystalline order or structure or due to the presence of small concentrations of foreign ions or lattice defects in an otherwise perfect crystal. Although there has been some experimentation in thermal-wave depth-profiling, (M. J. Adams and G. F. Kirkbright, Analyst 102, 678 (1977)) and A. Rosencwaig, J. Appl. Phys. 49, 2905 (1978)) this capability has not been extensively exploited, primarily because of the lack of adequate theoretical models. A recent model of Opsal and Rosencwaig, (J. Opsal and A. Rosencwaig, J. Appl. Phys. 53,4240 (1982)) (O-R model) shows how depth-profiling and multi-layer thickness analysis can be performed from thermal-wave measurements using either surface temperature or thermoacoustic probes, and allows for a fuller exploitation of this depth-profiling capability. There have also been several experimental impediments to thermal-wave profiling. For example, one would like, in many cases to operate outside of a photoacoustic cell, to employ a completely contactless method for thermal-wave generation and detection, and to couple thickness measurements with high spatial resolution, this last requirement necessitating the use of high-frequency ($>$100kHz) thermal waves.

SUMMARY OF INVENTION

Recently we have been able to satisfy all three requirements by employing a laser deflection technique whereby one laser is used for generating and another for detecting the thermal waves. In our method the heating and probe laser beams are focused and directed normal to the sample surface where they are slightly spaced apart. This is quite different than the conventional optical beam deflection technique where the probe beam skims over the surface of the sample as in (W. B. Jackson, N. M. Amer, A. C. Boccara and D. Fournier, Appl. Opt. 20 1333 (1981) and J. C. Murphy and L. C. Aamodt, Appl. Phys. Lett. 38, 196 (1981)).

Other features and advantages of the invention will become apparent from the following description read in conjunction with the attached drawings in which:

Figure 1:
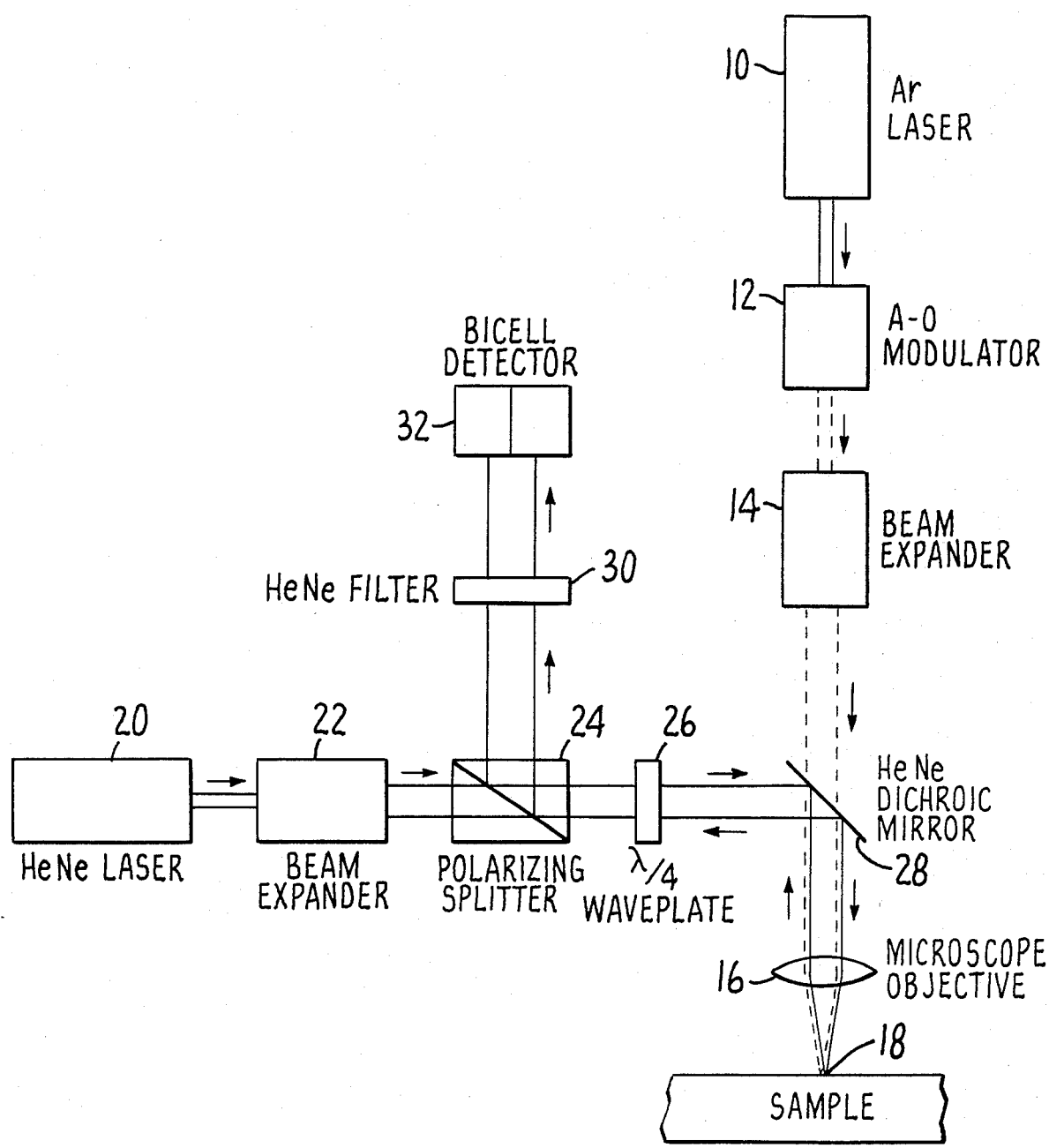
FIG. 1 is a diagram of a preferred form of apparatus of this invention for practice of the method of this invention.

Referring now in detail to the drawings, the heating apparatus illustrated therein includes a heating laser 10 which may be any convenient laser, such as Argon or carbon dioxide lasers and in actual experimental work a Lexel Model 75 Argon laser was used. The output of the laser 10 passes through a modulator 12 which may take any suitable form but in experimental work a modulator of Intra Action, Inc. was employed. The modulator should be operated at a frequency exceeding 10,000 cycles per second, and in the experimental work, modulation frequencies were used between 10,000 cycles per second and 10,000,000 cycles per second. The modulated laser beam passes through a beam expander 14 formed of a suitable lens system, and then a microscope objective lens 16 to be focused on a spot in an inspection area 18 when the film under inspection is positioned.

The detection apparatus in FIG. 1 includes a detection laser 20 which may take any suitable form, and in the work described herein, the detection laser was a Spectra Physics Model 120S helium/neon laser. The output beam of the detection laser 20 passes through a beam expander 22 and a polarizing splitter 24, quarter wave waveplate 26 to be reflected off a dichroic mirror 28 into the objective lens 16 and onto the inspection area 18. The optical elements are arranged so that the two focused laser beams are parallel but non-coaxial. In the work described herein the two beams were focused to spot sizes of between two and four microns with their center axes separated by approximately two microns. As explained hereinafter, the detection laser beam is reflected from the film being measured. The reflected beam is reflected from the dichroic mirror 28 and from the polarizing splitter 24 to a helium/neon filter 30 and a bicell detector 32.

The apparatus of FIG. 1 was operated for measurement of thin films of aluminum and silicon dioxide in the following way. The heating was provided from an Ar$^+$ ion laser whose beam was acousto-optically modulated at frequencies as high as 10MHz and with an incident peak power of approximately 30mW at the sample surface. The probe was an unmodulated 5mW He-Ne laser beam (2mW was incident on the sample surface) which was reflected off the sample surface and diverted by a polarizing beam splitter, in combination with a quarter-wave plate, onto a knife-edge (eg. bicell photodiode) detector. The probe beam undergoes periodic deflection of the order of $10^{-5}$-$10^{-4}$ radian by the thermal-wave induced changes in the local slope of the sample surface. This is analogous to the use of a laser probe for the detection of the surface acoustic waves, (R. L. Whitman and A. Korpel, Appl. Optics 8, 1567 (1969)) although here the surface deformation are due to the thermal waves. We were able to detect, at a 1MHz modulation frequency, changes in the local surface slope that resulted from local surface displacements of approximately $10^{-4}$ Å/$\sqrt{Hz}$, a sensitivity that is considerably greater than that reported in recent experiments done at much lower modulation frequencies with laser interferometry, (S. Ameri, E. A. Ash, V. Nueman and C. R. Petts, Electron. Lett. 17, 337 (1981)).

However, before we could combine the O-R model with our laser probe technique to perform quantitative thin-film thickness measurements, we had to extend it to three dimensions and to include thermoelastic surface deformations. In addition to three dimensional effects, and thermoelastic deflections, we found that in our experiments we also have to include thermal lens, optical effects, and nonlinear effects arising from the temperature dependence of the various material parameters.

The thermal lens effects (W. B. Jackson, N. M. Amer, A. C. Bocarra and D. Fournier, Appl. Opt. 20, 1333 (1981); J. C. Murphy and L. C. Aamodt, Apply. Phys. Lett. 38, 196 (1981) and R. L. Swofford, M. E. Long and A. C. Albrecht, J. Chem. Phys. 65, 179 (1979)) occur in the air above the sample surface and within any layer of the sample that is not optically opaque. Even though these thermal lenses have only micron-sized dimensions at the high modulation frequencies employed, their refractive power is still considerable since the normalized refractive index gradient, $n^{-1}(dn/dx) = n^{-1}(dn/dT)(dT/dx)$ across the lens is now quite high and of the same order as the thermal expansion coefficient of a solid. Also, even though the probe laser beam is incident normal to the sample surface, it strikes the thermal lens off-axis and thus undergoes refraction in both incident and reflected directions. Consequently, the theory predicts, and we find experimentally, that the thermal lens effect is appreciable for some materials such as Si.

Figure 2:
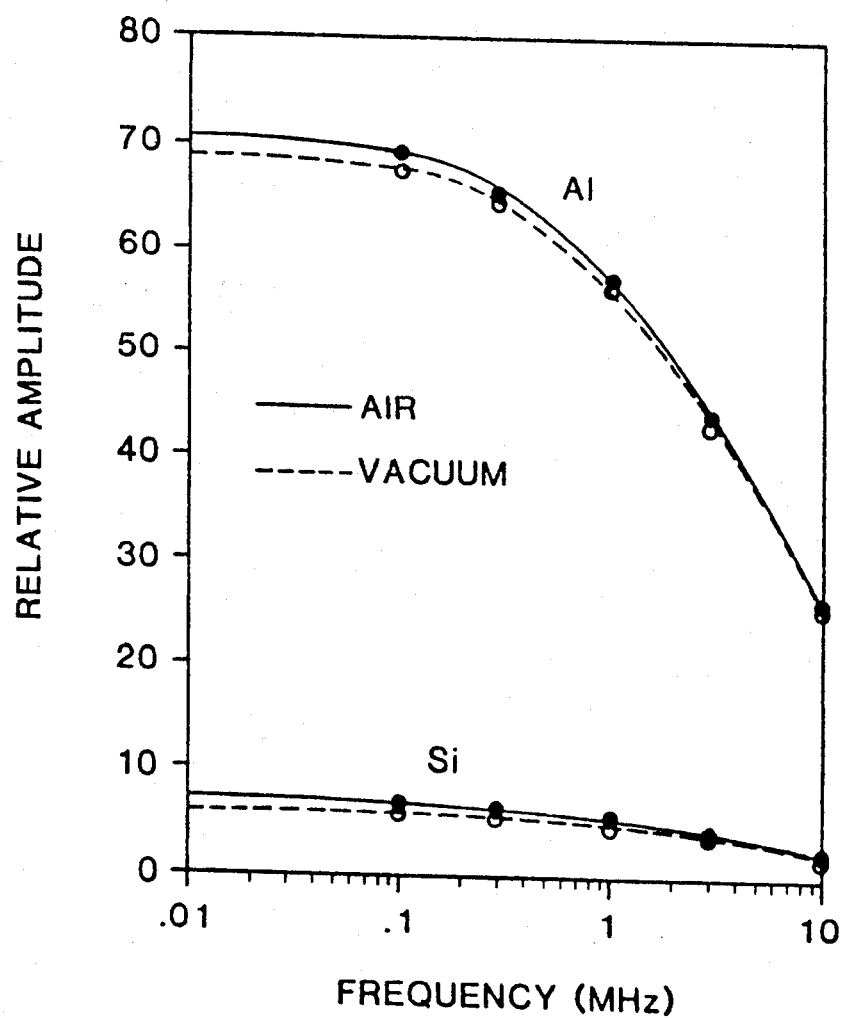
FIG. 2 is a frequency/response curve indicating the performance of the invention under operational conditions.

FIG. 2 presents comparisons with experiments for a complete calculation which includes optical reflectivities, finite absorption depths and finite probe beam diameters, under vacuum, where there is no thermal lens effect (dashed curves), and in air (solid curves). The agreement between theory and experiment is excellent.

In these thermal-wave experiments DC and AC temperature excursions can range from 30° C. to several hundred degrees depending on the sample's thermal characteristics. With such temperature excursions, the dependence on temperature of the various thermal, optical and elastic parameters has to be considered as well. In general, the most critical parameters appear to be the refractive index and the thermal conductivity. These temperature effects introduce appreciable nonlinearities in the model that cannot be neglected.

Optical effects will, of course, play an important role in these experiments as well. For example, in Si we have to take into account the optical absorption length ($\simeq 1$ $\mu$m) for the 488nm Ar+ ion laser light. Absorption and reflectivities must also be included. In addition, when dealing with optically transparent films such as $SiO_2$, optical interference effects within the film have to be included as well.

Figure 3:
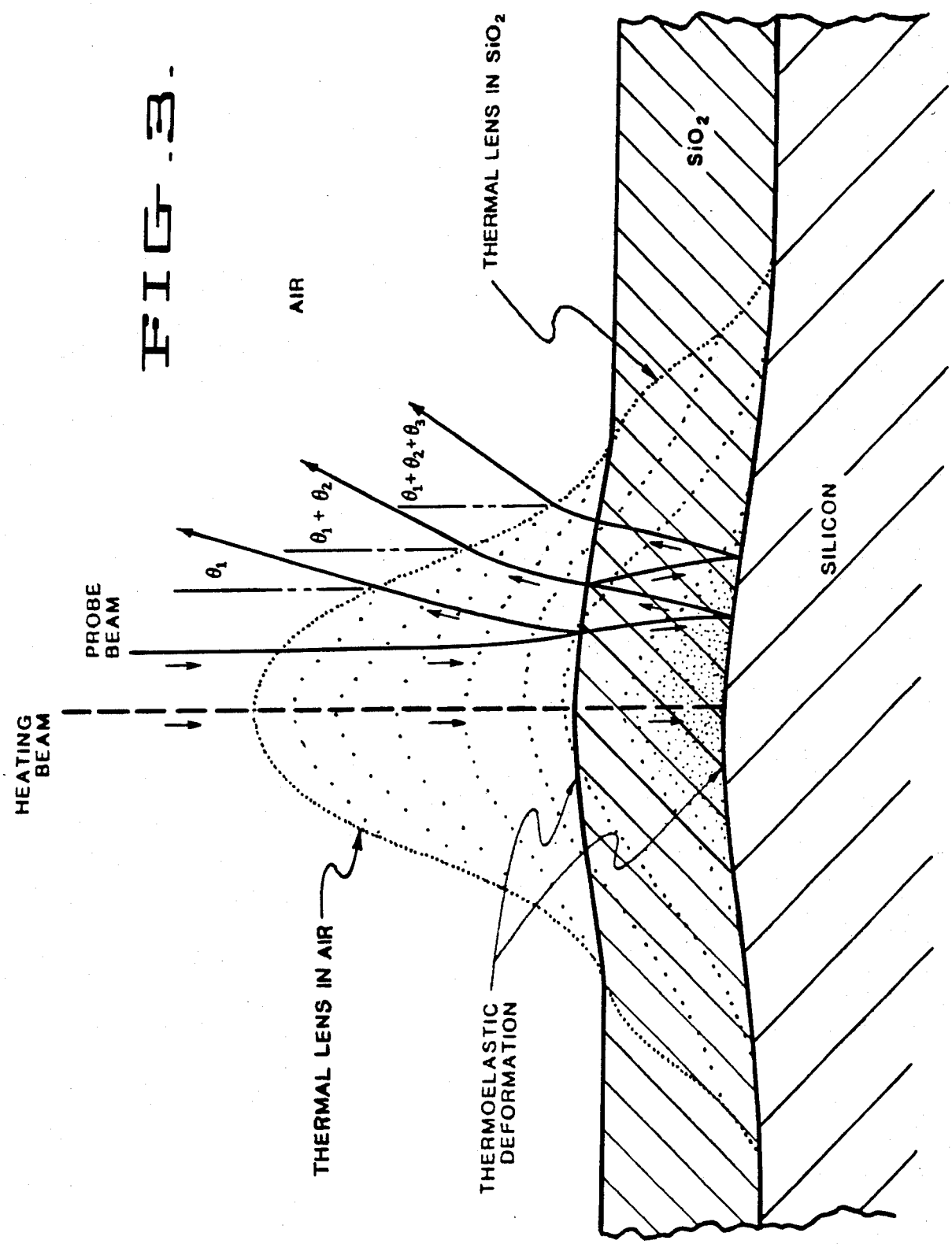
FIG. 3 is a diagram on a enlarged scale of the conditions at the inspection station of the apparatus of FIG. 1.

FIG. 3 schematically depicts the situation encountered for an $SiO_2$ film on Si. Here we see the thermoelastic deformations of both the Si-$SiO_2$ and the $SiO_2$-air surfaces, the thermal lenses in both the $SiO_2$ and the air, and the optical interference effects on the probe beam in the $SiO_2$ film. Note that the thermal lenses have opposite signs in air and $SiO_2$ because of the opposite signs of their respective dn/dT's.

Figure 4:
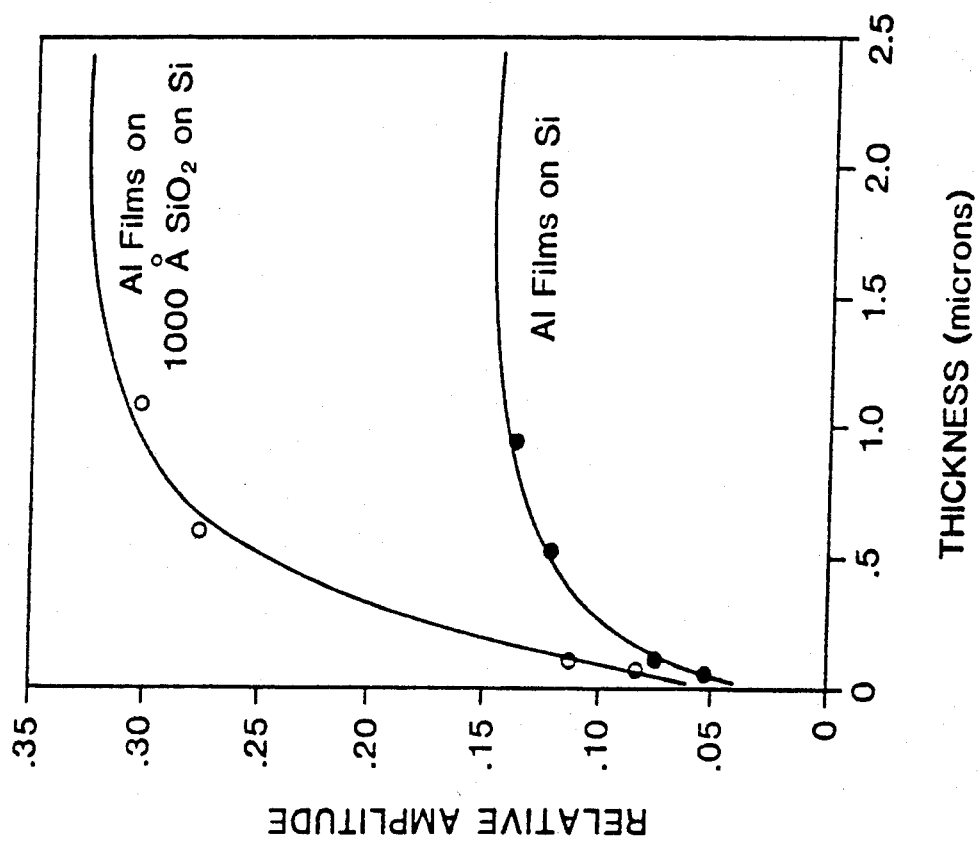
FIG. 4 is a thickness/amplitude plot showing performance results which the invention measuring aluminum films on silicon.

When all of the thermal lens, optical and nonlinear effects are properly included into the O-R model, we have a quantitative tool for measuring the thickness of thin films. This is illustrated in FIG. 4 where we show theoretical curves and data obtained for single films of Al on Si and for double films of Al and $SiO_2$ on Si. We have used the magnitude of the thermal-wave signal rather than the phase in these measurements, since the magnitude has a greater dynamic range and can be measured more precisely. The data in FIG. 4 are in excellent agreement with the theory both for the single and the double films. The precision of the reading obtained with a 1-sec averaging time translates to a thickness sensitivity of ±2% over the thickness range of 500 Å–25,000 Å for these films.

Figure 5:
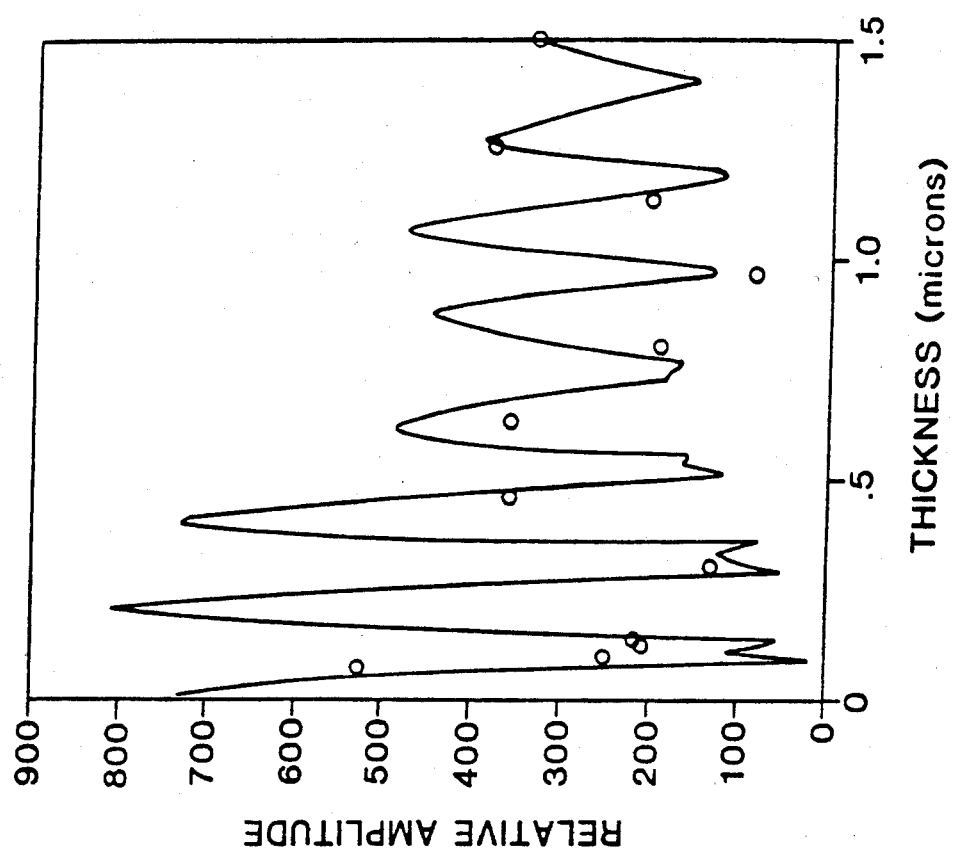
FIG. 5 is a similar thickness amplitude plot for a series of silicon dioxide on silicon films.

In FIG. 5 we show the theoretical curves and the data for a series of transparent $SiO_2$ films on Si. Although $SiO_2$ on Si is only a single film problem, the theory in this case must include thermoelastic deformations at both the Si-$SiO_2$ and $SiO_2$-air interfaces, thermal lens effects in both the $SiO_2$ and the air, and optical interference effects in the $SiO_2$ (see FIG. 3). The bit between theory and experiment is, with all this complexity, quite good, indicating that transparent as well as opaque films can be measured with this thermal-wave technique. The thickness sensitivity for $SiO_2$ films on Si appears to be ±2% over the range 500 Å–15,000 Å.

I claim:

1. A method for evaluating microscopic thermal features in a sample comprising:
   focusing an intensity modulated heating beam of energy at a microscopic spot on the surface of the sample to produce periodic thermal waves;
   focusing a probe beam of energy on a portion of the surface of the sample which is being periodically heated by the thermal waves, with said probe beam being substantially parallel to and laterally spaced from the heating beam; and
   monitoring the periodic angular displacement of the reflected probe beam, said periodic displacement resulting from the periodic angular changes in the surface conditions of the sample induced by the periodic thermal waves whereby the periodic angular displacement of the reflected probe beam can be used to evaluate microscopic thermal features in a sample.

2. The method of evaluating microscopic thermal features of claim 1 further including the step of modifying the evaluation to compensate for thermal air lens effects, thermal film lens effects, and optical absorption length.

3. A method for detecting thermal waves in a sample, said thermal waves being generated by a periodic heat source defined by an intensity modulated beam of energy comprising:
   focusing said intensity modulated heating beam of energy at a microscopic spot on the surface of the sample to produce periodic thermal waves;
   focusing a probe beam of energy on a portion of the surface of the sample which is being periodically heated by the thermal waves, with said probe beam being substantially parallel to and laterally spaced from the heating beam; and
   monitoring the periodic angular displacement of the reflected probe beam, said periodic angular displacement resulting from the periodic angular changes in the surface conditions of the sample induced by the periodic thermal waves whereby the periodic angular displacement of the probe beam can be used to detect the thermal waves in the sample.

4. The method of evaluating microscopic thermal features of claim 3 further including the step of modifying the evaluation to compensate for thermal air lens effects, thermal film lens effects, and optical absorption length.

5. An apparatus for evaluating microscopic thermal features in a sample comprising:
   a heating beam of energy;
   means for intensity modulating said heating beam;
   optical means for focusing the intensity modulated heating beam at a microscopic spot on the surface of the sample to generate periodic thermal waves;
   a probe beam of energy;
   means for directing the probe beam towards and through said optical means such that the heating and probe beams are directed along substantially parallel, noncoaxial paths, with said probe beam being focused on a portion of the surface of the sample which is being periodically heated by the thermal waves; and
   means for monitoring the periodic angular displacement of the reflected probe beam, said periodic displacement resulting from the periodic angular changes in the surface conditions of the sample induced by the periodic thermal waves whereby the periodic angular displacement of the reflected probe beams can be used to evaluate microscopic thermal features in a sample.

6. An apparatus as recited in claim 4 wherein the modulated heating beam is defined by a laser beam.

7. An apparatus as recited in claim 6 wherein the probe beam is defined by a laser beam.

8. An apparatus as recited in claim 7 wherein the wavelength of the optical output of the probe laser beam is different from the wavelength of the optical output of the heating laser beam.

9. An apparatus as recited in claim 8 wherein the means for directing the probe beam towards and through said optical means is defined by a dichroic mirror which reflects the probe laser beam while permitting the heating laser beam to pass therethrough.

10. An apparatus as recited in claim 5 further including a means for directing said reflected probe beam to said monitoring means.

11. An apparatus as recited in claim 10 wherein said means for directing said probe beam to said monitoring means is defined by a combination of a quarter wave plate and a polarizing beam splitter.

12. An apparatus as recited in claim 5 wherein said optical means is oriented to direct said intensity modulated heating beam substantially normal to the surface of the sample.

13. An apparatus for detecting thermal waves in a sample, said thermal waves being generated by a periodic heat source defined by an intensity modulated beam of energy comprising:
   means for focusing the intensity modulated heating beam at a microscopic spot on the surface of the sample to generate periodic thermal waves;
   a probe beam of energy;
   means for directing the probe beam towards and through said optical means such that the heating and probe beams are directed along substantially parallel, noncoaxial paths, with said probe beam being focused on a portion of the surface of the sample which is being periodically heated by the thermal waves; and
   means for monitoring the periodic angular displacement of the reflected probe beam, said periodic displacement resulting from the periodic angular changes in the surface conditions of the sample induced by the periodic thermal waves whereby the periodic angular displacement of the reflected probe beam can be used to detect the thermal waves in the sample.

14. An apparatus as recited in claim 13 wherein the modulated heating beam is defined by a laser beam.

15. An apparatus as recited in claim 14 wherein the probe beam is defined by a laser beam.

16. An apparatus as recited in claim 15 wherein the wavelength of the optical output of the probe laser beam is different from the wavelength of the optical output of the heating laser beam.

17. An apparatus as recited in claim 16 wherein means for directing the probe beam towards and through said optical means is defined by a dichroic mirror which reflects the probe laser beam while permitting the heating laser beam to pass therethrough.

18. An apparatus as recited in claim 13 further including a means for directing said reflected probe beam to said monitoring means.

19. An apparatus as recited in claim 18 wherein said means for directing said probe beam to said monitoring means is defined by a combination of a quarter wave plate and a polarizing beam splitter.

20. An apparatus as recited in claim 13 wherein said optical means is oriented to direct said intensity modulated heating beam substantially normal to the surface of the sample.

* * * * *